United States Patent [19]

Grabstein et al.

[11] Patent Number: 5,162,111
[45] Date of Patent: Nov. 10, 1992

[54] TREATMENT OF BACTERIAL DISEASES WITH GRANULOCYTE-MACROPHAGE COLONY STIMULATING FACTOR

[76] Inventors: Kenneth H. Grabstein, 5829 NE. 75th St., No. 443, Seattle, Wash. 98115; Philip J. Morrissey, 4412 - 153rd Ave. SE., Bellevue, Wash. 98006

[21] Appl. No.: 892,123

[22] Filed: Jul. 30, 1986

[51] Int. Cl.$^5$ .............................................. A61K 37/02
[52] U.S. Cl. ........................................ 424/85.1; 514/8; 514/2; 424/92; 530/395; 530/351; 930/145
[58] Field of Search ...................... 514/8, 21; 530/395, 530/351; 424/85.1

[56] References Cited

U.S. PATENT DOCUMENTS

4,621,050  11/1986  Sugimoto ......................... 430/172.2

FOREIGN PATENT DOCUMENTS

0118915   9/1984  European Pat. Off.
61-04506  8/1986  Japan.
WO8600639 1/1986  PCT Int'l Appl.

OTHER PUBLICATIONS

Donahue et al, *Blood* 66(6) 1985, pp. 479–481.
Seiff et al, *Science* 230, 1985, pp. 1171–1173.
Handman and Burgess, "Stimulation by granulocyte--macrophage colony-stimulating factor of *Leishmania tropica* killing by macrophages," *J. Immunol.* 122:1223 (1979).
Nozawa et al., "Stimulation by conditioned medium of L-929 fibroblasts, *E. coli* lipopolysaccharide, and muramyl dipeptide of candidacidal activity of mouse macrophages," *Cell. Immunol.* 53:116 (1980).
Ralph et al., "Colony-stimulating factors and regulation of macrophage tumoricidal and microbicidal activities," *Cell. Immunol.* 76:10 (1983).
Weisbart et al., "Human granulocyte-macrophage colony-stimulating factor is a neutrophil activator," *Nature* 314:361 (1985).
Fleischmann et al., "Granulocyte-macrophage colony-stimulating factor enhances phagocytosis of bacteria by human neutrophils," *Blood* 68:708 (1986).
Mayer et al., "Recombinant human GM-CSF induces leukocytosis and activates peripheral blood polymorphonuclear neutrophils in nonhuman primates," *Blood* 70:206 (1987).
Burgess and Metcalf, "The Nature and Action of Granulocyte-Macrophage Colony Stimulating Factors", *Blood* 56:947 (1980).
Gasson et al., "Purified Human Granulocyte-Macrophage Colony-Stimulating Factor: Direct Action on Neutrophils", *Science* 226:1339 (1984).
Weisbart et al., "Human Granulocyte-Macrophage Colony-Stimulating Factor is a Neutrophil Activator", *Nature* 314:361 (1985).
Cantrell et al., "Cloning, Sequence, and Expression of a Human Granulocyte/Macrophage Colony-Stimulating Factor", *Proc. Natl. Acad. Sci. U.S.A.* 82:6250 (1985).
Metcalf et al., "Biologic Properties In Vitro of a Recombinant Human Granulocyte-Macrophage Colony-Stimulating Factor", *Blood* 67:37 (1986).
Metcalf, "The Molecular Biology and Functions of the Granulocyte-Macrophage Colony-Stimulating Factors", *Blood* 67:257 (1986).
Grabstein et al., "Induction of Macrophage Tumoricidal Activity by Granulocyte-Macrophage Colony-Stimulating Factor", *Science* 232:506 (1986).

*Primary Examiner*—Garnett D. Draper
*Attorney, Agent, or Firm*—Christopher L. Wight; Scott G. Hallquist

[57] ABSTRACT

Subjects suffering from infectious diseases are treated by direct administration of therapeutically-effective quantities of granulocyte-macrophage colony stimulating factor employed by itself or in conjunction with an antibiotic or a sulfonamide or other immunologically effective therapeutic agents. Homogeneous granulocyte-macrophage colony stimulating factor for use in treatment in bacterial diseases is prepared by recombinant DNA techniques and then purified to homogeneity by reverse phase high-performance liquid chromatography so that it may be safely administered to subject's suffering from infectious diseases.

16 Claims, 8 Drawing Sheets

```
                                                    5' --AAAGTTCTCTGGAGG    -1
                                                            SfaN I
human   ATG TGG CTG CAG AGC CTG CTG CTC TTG GGC ACT GTG GCC TGC AGC ATC TCT GCA CCC GCC   60
        Met Trp Leu Gln Ser Leu Leu Leu Leu Gly Thr Val Ala Cys Ser Ile Ser Ala Pro Ala    3
                                                                          *
mouse                                                   Ser Leu Ser Ala Pro Thr    3
                                                        AGC CTC TCA GCA CCC ACC   18

CGC TCG CCC AGC CCC AGC ACA CAG CCC TGG GAG CAT GTG AAT GCC ATC CAG GAG GCC CGG  120
        Arg Ser Pro Ser Pro Ser Thr Gln Pro Trp Glu His Val Asn Ala Ile Gln Glu Ala Arg   23

Arg Ser Pro Ile Thr Val Thr Arg Pro Trp Lys His Val Glu Ala Ile Lys Glu Ala ...   22
        CGC TCA CCC ATC ACT GTC ACC CGG CCT TGG AAG CAT GTA GAA GCC ATC AAA GAA GCC ...   75
                                    Nci I

CGT CTC CTG AAC CTG AGT AGA GAC ACT GCT GCT GAG ATG AAT GAA ACA GTA GAA GTC ATC  180
        Arg Leu Leu Asn Leu Ser Arg Asp Thr Ala Ala Glu Met Asn Glu Thr Val Glu Val Ile   43

... ... Leu Asn Leu Leu Asp Asp Met Pro Val Thr Leu Asn Glu Glu Val Glu Val Val   40
        ... ... CTG AAC CTC CTG GAT GAC ATG CCT GTC ACA TTG AAT GAA GAG GTA GAA GTC GTC  129

TCA GAA ATG TTT GAC CTC CAG GAG CCG ACC TGC CTA CAG ACC CGC GTG GAG CTG TAC AAG  240
        Ser Glu Met Phe Asp Leu Gln Glu Pro Thr Cys Leu Gln Thr Arg Val Glu Leu Tyr Lys   63

Ser Asn Glu Phe Ser Phe Lys Lys Leu Thr Cys Val Gln Thr Arg Leu Lys Ile Phe Glu   60
        TCT AAC GAG TTC TCC TTC AAG AAG CTA ACA TGT GTG CAG ACC CGC CTG AAG ATA TTC GAG  208

CAG GGC CTG CGG GGC AGC CTC ACC AAG CTC AAG GGC CCC TTG ACC ATG ATG GCC AGC CAC  300
        Gln Gly Leu Arg Gly Ser Leu Thr Lys Leu Lys Gly Pro Leu Thr Met Met Ala Ser His   83

Gln Gly Leu Arg Gly Asn Phe Thr Lys Leu Lys Gly Ala Leu Asn Met Thr Ala Ser Tyr   80
        CAG GGT CTA CGG GGC AAT TTC ACC AAA CTC AAG GGC GCC TTG AAC ATG ACA GCC AGC TAC  268

TAC AAA CAG CAC TGC CCT CCA ACC CCG GAA ACT TCC TGT GCA ACC CAG ATT ATC ACC TTT  360
        Tyr Lys Gln His Cys Pro Pro Thr Pro Glu Thr Ser Cys Ala Thr Gln Ile Ile Thr Phe  103

Tyr Gln Thr Tyr Cys Pro Pro Thr Pro Glu Thr Asp Cys Glu Thr Gln Ala Thr Thr Tyr  100
        TAC CAG ACA TAC TGC CCC CCA ACT CCG GAA ACG GAC TGT GAA ACA CAA GCT ACC ACC TAT  328

GAA AGT TTC AAA GAG AAC CTG AAG GAC TTT CTG CTT GTC ATC CCC TTT GAC TGC TGG GAG  420
        Glu Ser Phe Lys Glu Asn Leu Lys Asp Phe Leu Leu Val Ile Pro Phe Asp Cys Trp Glu  123

Ala Asp Phe Ile Asp Ser Leu Lys Thr Phe Leu Thr Asp Ile Pro Phe Glu Cys Lys Lys  120
        GCG GAT TTC ATA GAC AGC CTT AAA ACC TTT CTG ACT GAT ATC CCC TTT GAA TGC AAA AAA  388

CCA GTC CAG GAG TGA GACCGGCCAGATGAGGCTGGCCAAGCCGGGGAGCTGCTCTCTCATGAAACAAGAG--3'  490
        Pro Val Gln Glu End                                                              127

Pro Val Gln Lys End        ┌Hae II
        CCA GTC CAA AAA TGA GGAAGCCCAGGCCAGCTCTGAATCCAGCTTCTCAGACTGCTGCTTTTGTGCCTGC--3'  124
                                                                                         458
```

*Fig. 2.*

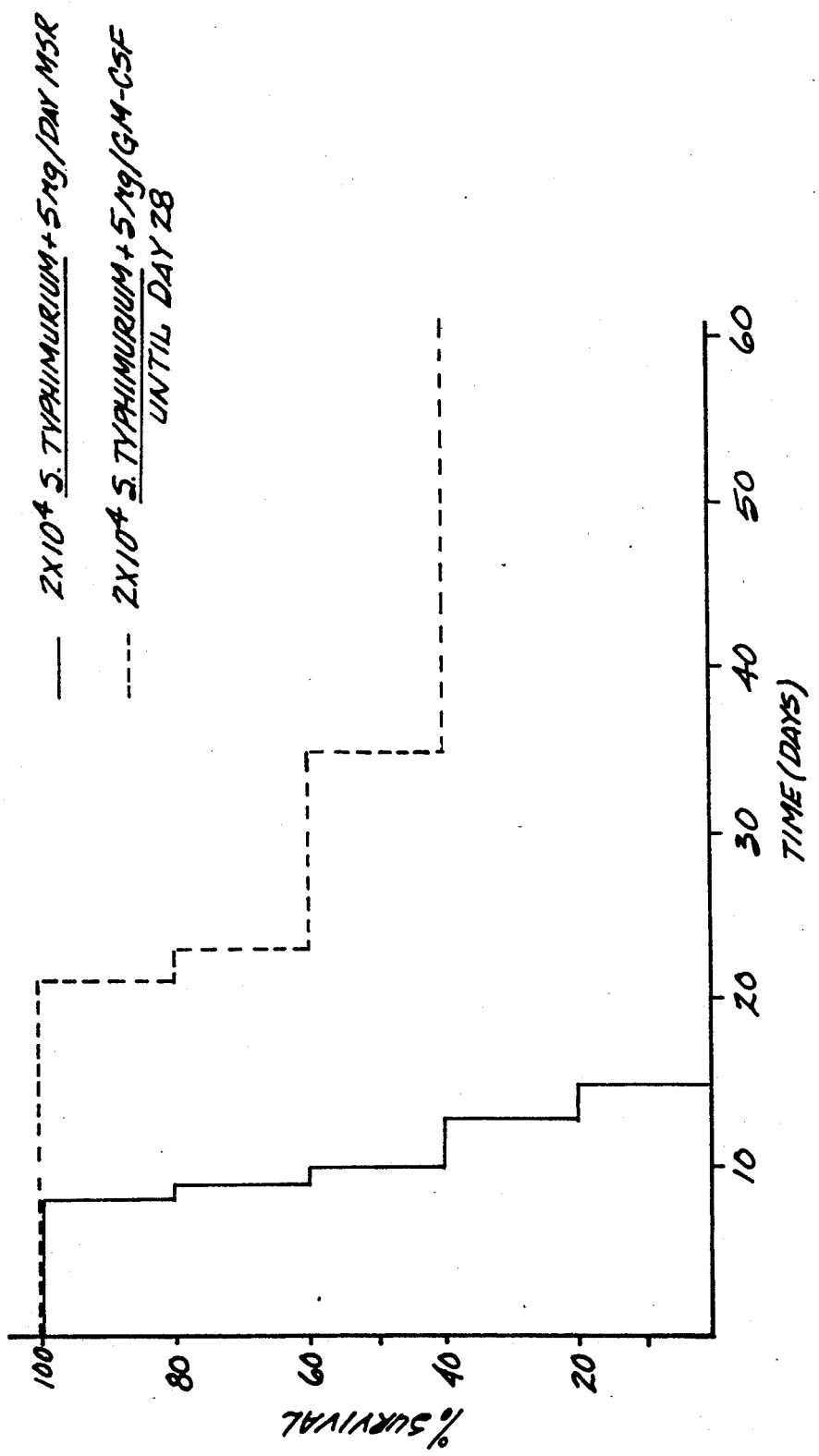

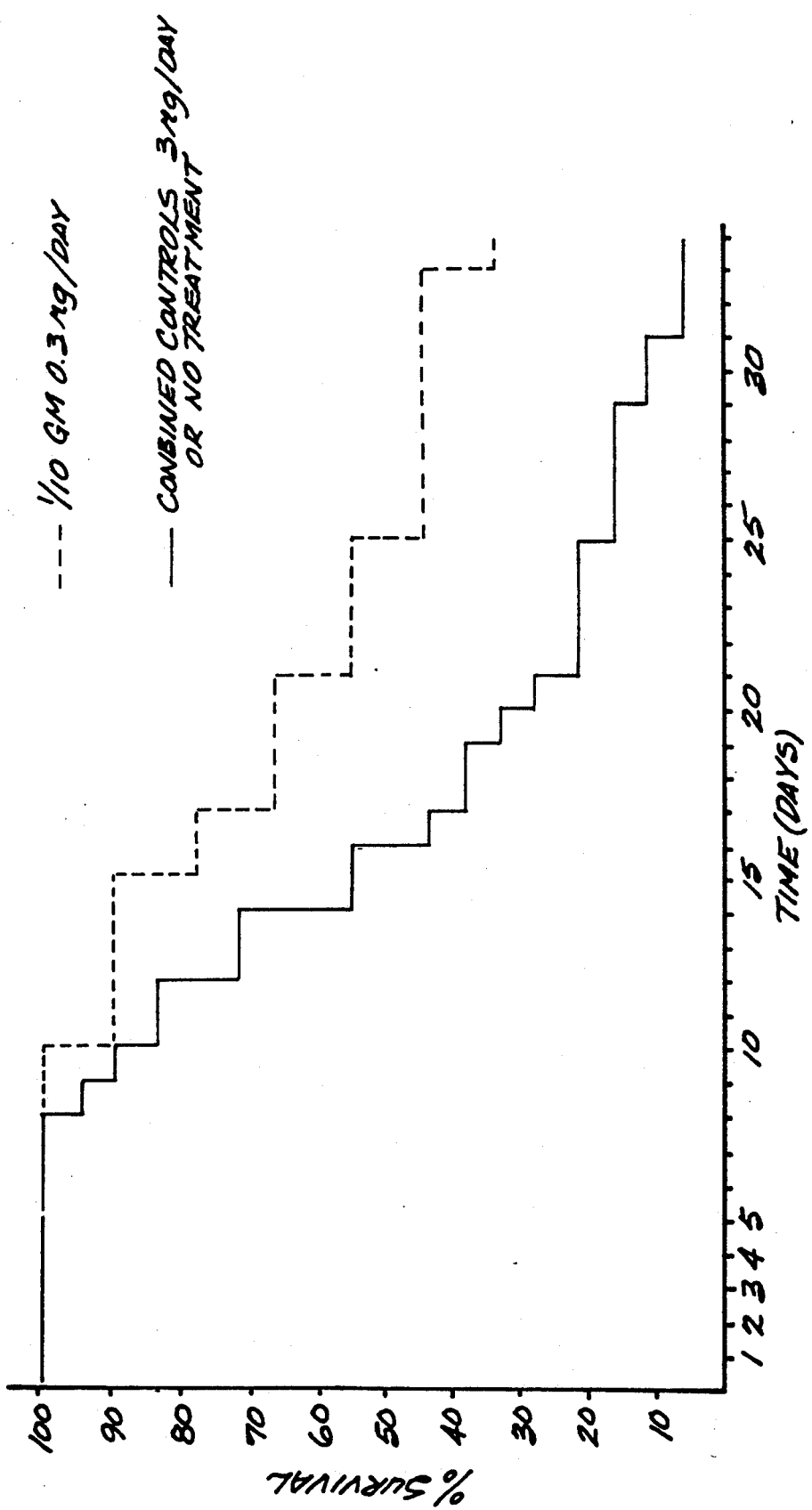

Fig. 8. EFFECT OF GM-CSF ON BODY LOAD OF S. TYPHIMURIUM

AVERAGE NUMBER OF COLONIES IN 10 ml PERITONEAL WASH

| | DAY2 | DAY3 | DAY4 | DAY7 |
|---|---|---|---|---|
| 5μg GM/DAY | 8 | 32 | 24 | 10 |
| 5μg MSA/DAY | 5 | 221 | 85 | 110 |

AVERAGE NUMBER OF COLONIES/SPLEEN

| | | | | |
|---|---|---|---|---|
| 5μg GM/DAY | 2,510 | 2,920 | 7,050 | 14,250 |
| 5μg MSA/DAY | 2,730 | 18,150 | 48,000 | 213,900 |

AVERAGE NUMBER OF COLONIES/LIVER

| | | | | |
|---|---|---|---|---|
| 5μg GM/DAY | 1,850 | 3,800 | 2,940 | 2,100 |
| 5μg MSA/DAY | 2,050 | 9,500 | 8,400 | 59,500 |

| AMOUNT OF GM-CSF/DAY | AVERAGE NUMBER OF S. TYPHIMURIUM/SPLEEN $\times 10^{-2}$ |
|---|---|
| 0 | 215 |
| 10 mg | 57 |
| 1 mg | 71 |
| 0.1 mg | 117 |
| 0.01 mg | 116 |

Fig. 9.

TREATMENT OF BACTERIAL DISEASES WITH GRANULOCYTE-MACROPHAGE COLONY STIMULATING FACTOR

TECHNICAL FIELD

The present invention relates to the treatment of infectious diseases, and more particularly to the treatment of bacterial diseases with granulocyte-macrophage colony stimulating factor ("GM-CSF").

Background of the Invention

Bacterial infections for centuries have been and still are a commonplace result of many diseases. Numerous types of bacterial infectious disease exist including various coccus diseases, for example, staphylococcal infections, streptococcal infections (including rheumatic fever and chorea), pneumococcal infections, meningitis and gonorrhea. Also common are the different types of bacilli bacterial diseases, including: those caused by grampositive bacilli, for instance erysipeloid, diphtheria, nocardiosis and actinomycosis; and, those caused by gram-negative anaerobic bacilli, including salmonella infections, (e.g., typhoid fever), shigellosis, pseudomonas and cholera. Other common infectious diseases include various mycobacterial diseases, for instance tuberculosis, leprosy, and spirochetes caused diseases, including syphilis.

Preexisting diseases or suppression of the immune system cause the body to be susceptible to "opportunistic" infectious diseases which otherwise might not occur. For instance, diabetics suffer from a propensity to numerous infections, at least in part caused by defective leukocyte function. Also, radiation or chemotherapeutic treatment of patients suffering from neoplasms result in severe damage to hematopoietic stem cells often causing such patients to fall prey to common infectious diseases which otherwise would be resisted. In addition, the immune system of patients suffering from acquired immune deficiency syndome is often suppressed to the level that common types of infections cannot be countered by the immune system, leading to eventual death. Common types of infectious diseases which occur in patients with diminished immune system capacity include, for example, pseudomonas infections and streptococcus.

Infectious bacterial diseases are typically treated with antibiotics or sulfonamides. Such antibiotics may include: penicillins, including pencillin G, penicillin V and ampicillin; cephalosporins; aminoglycosides, including gentamicin and streptomycin; tetracyclines; macrolides, including erythromycin; chloramphenicol; clindamycin and vancomycin. Common sulfonamides include sulfadiazine, sulfisoxazole, sulfachlorpyridazine, sulfamethoxazole, etc.

Although antibiotic and sulfonamide treatment of infectious diseases has resulted in the saving of countless lives, such treatment does have significant limitations and suffers from serious drawbacks. For instance, the various kinds of antibiotics and sulfonamides are typically effective against only a limited type or cause of infection. Thus, if the actual cause of the infection is unknown, trial and error may be required before an effective antibiotic/sulfonamide is selected. During this time period the infection may rage unchecked. Also, use of antibiotics/sulfonamides increases selective pressure for mutants resistant to the antibiotic/sulfonamide. As a result, not infrequently the antibiotic/sulfonamide eventually becomes ineffective, especially if employed against a chronic infectious disease.

Another drawback of antibiotics/sulfonamides is that they may be toxic to the patient. A further limitation of antibiotics/sulfonamides is that they are not capable of disposing the dead bacteria and the side effects resulting from the infectious disease.

SUMMARY OF THE INVENTION

The present invention concerns employing lymphokine GM-CSF to treat infectious diseases. GM-CSF is a glycoprotein that is believed to induce precursor stem cells found in the bone marrow to proliferate and differentiate into granulocyte and macrophage haematopoietic cells. Specifically GM-CSF has been found to stimulate precursor cells to form colonies of granulocytes and precursor macrophages in semisolid culture media.

In accordance with the present invention, GM-CSF is administered to a subject suffering from an infectious disease. The GM-CSF may be used by itself, in conjunction with an antibiotic or a sulfonamide, or in combination with other immunologically effective therapeutic agents, such as interleukin 1, interleukin 2, or a species of interferon. The GM-CSF may be administered in any convenient manner, including by various parenteral methods. The dosage of the GM-CSF will depend upon various factors, such as the specie of the subject being treated, the condition of the subject being treated, and the type of bacterial infection being treated. In general, the GM-CSF may be administered in doses of from about 0.05–500 micrograms per kilogram (ug/kg) of body weight of the subject.

The present invention also concerns the production of purified recombinant GM-CSF for use in the treatment of bacterial diseases. In the production procedures, the gene encoding GM-CSF is isolated from a cDNA library constructed by reverse transcription of polyadenylated mRNA isolated from total RNA extracted from cell lines or the other potential sources of GM-CSF. Alternatively, the GM-CSF gene is chemically synthesized as a single unit or in fragments which are then ligated together to form the complete gene. The GM-CSF gene is then inserted into an appropriate expression vector, which is used to transform a host cell to direct production of mature functional GM-CSF. The expressed GM-CSF is then purified to remove impurities so that it may be safely administered to subjects suffering from infectious diseases.

BRIEF DESCRIPTION OF THE DRAWINGS

The details of a typical embodiment of the present invention will be described in connection with the accompanying drawings, in which:

FIG. 2, containing two sheets, illustrates the nucleic acid sequence and the corresponding amino acid sequence of the human and murine GM-CSF genes contained in the nucleotide fragments depicted in FIG. 1, with the nucleotides being numbered from the beginning of the coding sequences of the genes and the amino acids being numbered from the mature $NH_2$-terminus of the proteins, i.e., the Ala residues marked with an asterisk, to the termination codons TGA;

FIGS. 6 and 7 illustrate the ability of GM-CSF to counteract the infection of murine subjects with lethal doses of *Salmonella typhimurium* ("*S. typhimurium*"); and FIGS. 8 and 9 illustrate the result of in vitro studies ascertaining the number of S. typhimurium microorganisms present in various organs of mice inoculated with lethal doses of S. typhimurium and then treated with GM-CSF.

DETAILED DESCRIPTION

Therapeutic Studies

Figure 1:
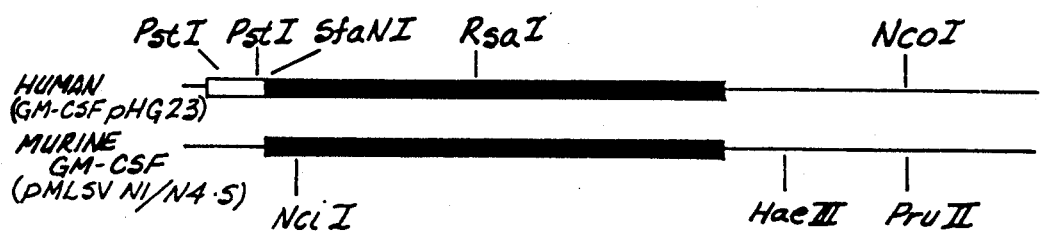
FIG. 1 illustrates a partial restriction map of cDNAs containing the human and murine GM-CSF genes.

The ability of GM-CSF to treat infectious diseases is ascertained by in vivo and in vitro studies. In the in vivo studies, animal models are inoculated with a lethal dose of bacteria and then treated with purified recombinant GM-CSF in hopes of enhancing the survival of the models. Dose responses can be investigated by treating the models with various amounts of purified recombinant GM-CSF to ascertain differences in survival rate based on the dosages. As a control, some of the models are either not treated at all or "treated" with serum albumen.

The in vitro studies investigate the number of bacterial cells present in certain body tissues of animals inoculated with lethal doses of bacteria and then subsequently treated with GM-CSF. In one such study, models are treated with GM-CSF on a daily basis. The animals were sacrificed periodically and various organs harvested. Single cell suspensions of some of the organs are prepared and plated in agar conducive to the growth of the bacteria. The number of bacterial colonies which grow in the agar will be proportional to the number of such bacterial cells which are present in the various organs. This type of in vitro investigation can be conducted with various dosages of GM-CSF to ascertain the efficacy of GM-CSF based on the quantity of GM-CSF employed.

Various types of bacteria may be employed as an infectious agent in the in vivo and in vitro studies, including those types of bacteria discussed above. As an illustrative but nonlimiting example, a specie of pasteurella, for example, *pasteurella multiocida* or *pasteurella haemolytica*, may be employed for studies involving bovine, porcine, ovine or equine animals or poultry animals such as chickens and turkeys. This bacteria causes a respiratory disease which has been implicated in the etiology of "shipping fever" syndrome, a common cause of animal death which occurs during transit of animals. As a further illustrative but not limiting example, for therapeutic studies involving rat or murine subjects, various species of salmonella or shigella may be employed. Such species include, for example, *S. typhimurium, Salmonella dublin, Salmonella abortusovis, Salmonella abortivoequina, Salmonella gallinarum, Salmonella choleraesuis, Salmonella typhi, Shigella flexneri,* and *Shigella sonnei.*

As a specific but not limiting example, the ability of GM-CSF to effectively treat mice infected with lethal doses of *S. typhimurium* is set forth in Examples 1 through 4 below. These studies show the treatment of mice infected with *S. typhimurium* with purified recombinant murine GM-CSF enhanced prolongation of life and long-term survival of the mice. Also, treated mice were found to have fewer *S. typhimurium* microorganisms in their various organs than did control group animals which were either not treated or received doses of mouse serum albumen. These studies illustrate the efficacy of GM-CSF as an anti-infective agent.

The studies detailed in Examples 1 and 2 below include in vivo investigations wherein mice are infected with lethal doses of *S. typhimurium.* Such mice are then treated with daily doses of GM-CSF. A control group of mice are either untreated or given doses of mouse serum albumen. In the studies, the control group animals died within a short period of time; however, in a substantial number of the treated animals, length of life was prolonged with about 40% of the animals actually surviving the lethal doses of *S. typhimurium.*

The therapeutic studies delineated in Examples 3 and 4 concerned mice that are infected with lethal doses of *S. typhimurium* and then treated with GM-CSF. A control group of animals are either not treated or receive doses of mouse serum albumen. The doses range from 0.01 to 10 microgram (ug) of purified GM-CSF per injection in mice weighing approximately 20 g. This equates to a dosage of from 0.5 to 500 ug/kg of body weight. After a period of time, the animals are sacrificed and their organs harvested. Individual cell suspensions are prepared and then plated in agar to ascertain the quantity of *S. typhimurium* present by the number of colonies that form in the agar. The test results showed that animals treated with GM-CSF had fewer *S. typhimurium* in their organs than did the control group animals.

These studies illustrate the efficacy of GM-CSF as an antiinfective agent. The particular pathway by which GM-CSF eliminates infection has not been fully elucidated; applicants hypothesize that several possible explanations or combination of explanations may exist. Perhaps the GM-CSF causes increased proliferation and differentiation of monocytes into macrophages so that more macrophages are available to counteract the infection. As a second possibility, perhaps the GM-CSF provides a signal whereby macrophages are summoned from the blood stream in other locations in the body to the site of infection. However, these possibilities would seem to be inconsistent with the knowledge that *S. typhimurium* bacteria generally survive phagocytosis and even multiply within phagocytic cells.

As a further alternative, the GM-CSF may cause macrophages and/or granulocytes to function more efficiently, especially in killing bacteria. In this potential pathway, the GM-CSF may induce the macrophages and/or granulocytes into cytolytic activity against bacteria infected cells (or the bacteria themselves in the case of granulocytes) rather than relying on the phagocytic capabilities of the macrophage.

It will be appreciated that the ability to treat infectious diseases by using GM-CSF to promote host immune response has several potential significant advantages. For example, this type of treatment could be used alone or in conjunction with antibiotic treatment. Moreover, unlike antibiotic treatments, GM-CSF treatment would not be limited to a particular type or cause of infection, but rather should be effective against virtually all types and causes of bacterial infections. In addition, GM-CSF treatment would facilitate the removal of dead bacterial cells from the body and could assist in reducing side effects caused by the infectious disease, including reduction of fever, fluid retention, etc. Further, it appears that GM-CSF treatment would be effective against pathogens that typically survive phagocytosis, for example, *S. typhimurium, turbercle basilli* and *leprosy basilli.*

Therapeutic Applications

Based on the foregoing therapeutic studies, recombinant GM-CSF can be employed to treat bacterial infections. It can be used by itself or in conjunction with antibiotics, such as those discussed above, or in combination with other immunologically effective therapeutic agents, for instance interleukin 1, interleukin 2 and various species of interferons.

Recombinant GM-CSF can be administered to a subject in need of treatment by a variety of conventional parenteral routes. In general, the recombinant GM-CSF may be administered in dosages of about 0.05 to 500 ug/kg of body weight of the subject per day. Some variation in dosage will necessarily occur depending upon the condition of the subject being treated, the stage of the infection, the cause of the infection, etc.

The recombinant GM-CSF may be administered alone or in combination with pharmaceutically acceptable carriers and either in single or multiple doses. Suitable pharmaceutical carriers include inert solid diluents or fillers, sterile aqueous solutions and various nontoxic organic solvents. The pharmaceutical compositions formed by combining the recombinant GM-CSF with the pharmaceutically acceptable carrier are then readily administered in a variety of dosage forms, such as injectible solutions, inhalable aerosols, suppositories, and the like. These pharmaceutical compositions can, if desired, contain additional ingredients such as binders, excipients, and the like.

For parenteral administration, solutions of the recombinant GM-CSF in sesame or peanut oil or in aqueous propylene glycol may be employed, as well as sterile nontoxic, nonallergic solutions of distilled water, human serum albumen, Ringer's solution, Hank's solution, etc. Such solutions could be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the various aforementioned sterile aqueous media that may be employed are all readily preparable by standard techniques well known to those skilled in the art.

Recombinant GM-CSF in the various formats discussed above may be administered to animal subjects suffering from a wide variety of infectious diseases, including those delineated above. Such subjects may include not only humans, but bovine, porcine, ovine and equine animals. The subjects may also include poultry animals such as chickens, rabbits and turkeys. Of course, the specie of GM-CSF employed must be compatible with the animal specie being treated, i.e., the specie of GM-CSF must be from the same specie of the animal being treated.

Cloning of Recombinant GM-CSF Gene

GM-CSF is produced only in minute quantities in vivo. Accordingly, relatively large amounts of highly purified GM-CSF for use in therapeutic treatments of infection in accordance with the present invention is produced through recombinant techniques. A discussion of recombinant DNA techniques in general is set forth in the editorial and supporting papers in Vol. 196 *Science* (April 1977). Also, the preparation of recombinant murine and human GM-CSF is discussed in U.S. patent applications, Ser. Nos. 666,041 and 750,401, which applications are assigned to the same assignee to which the present application is assigned. These two U.S. patent applications are incorporated herein by reference. The production of recombinant murine and human GM-CSF is also detailed in a technical publication by applicants and co-researchers, Cantrell et al., *Proc. Natl. Acad. Sci.* (USA) 82:6250–6254 (1985), incorporated herein by reference.

In the recombinant DNA techniques discussed in the above references, the gene coding for GM-CSF is isolated from a cDNA library, for instance with a labeled DNA or RNA probe. The labeled probe may correspond to a portion of the amino terminal sequence or other portion of the GM-CSF gene. The probe may be prepared by various techniques, including by chemical synthesis. As an alternative, the probe may consist of a portion of or the entire homologous GM-CSF gene of another animal specie. This homologous probe may itself be derived from a cDNA library of the other animal specie by use of a synthetic oligonucleotide probe corresponding to a portion of the nucleotide sequence of the GM-CSF gene for such other specie.

To prepare the cDNA library, for instance from a human source, total RNA is extracted from lymphoma cell lines, such as HUT-102, Jurkat or HL60, or from other potential types of sources of GM-CSF RNA, such as human peripheral blood mononuclear cells. As another example, the molecular clone of the murine GM-CSF gene is derived from total RNA extracted from murine cell lines thought to produce GM-CSF, such as various T-cell and macrophage cell lines, including the T-lymphoma cell line LRBM-33 or clones thereof, which are radiation-induced splenic lymphoma cell lines from the B-10.BR mouse. Total RNA is extracted from the above cell lines by standard methods, for instance, by the use of guanidium thiocyanate, together with a reducing agent, such as 2-mercaptoethanol, as discussed by Chirgwin et al., *Bio. Chem.* 18:5294 (1979); and, Maniatis et al., *Molecular Cloning A Laboratory Manual*, Cold Spring Harbor Laboratory, Cold Spring Harbor, N.Y. (1982). The RNA is isolated from the protein by common techniques, such as phenol/chloroform extraction, ethanol precipitation or sedimentation through cesium chloride. Thereafter, polyadenylated mRNA is separated from the extracted protein by well-known procedures, such as by chromatography on oligo (dT)-cellulose as described by Edmonds et al., *Proc. Natl. Acad. Sci.* (USA) 68:1336 (1971); Aviv and Leader, *Proc. Natl. Acad. Sci.* (USA) 69:1408 (1972); and, Maniatis et al., supra at 197. A cDNA library is constructed by reverse transcription of the polyadenylated mRNA with the enzyme avian myeloblastosis virus ("AMV") reverse transcriptase to form an initial cDNA strand by using the mRNA as a template. The DNA is rendered double-stranded with DNA polymerase I, RNase and *Escherichia coli* ("*E. coli*") DNA ligase.

The double-stranded cDNA is inserted within the appropriate cloning vector to transform compatible eukaryotic or prokaryotic host cells for replication of the vector. Various types of cloning vectors may be utilized. Although the preference is for plasmid, the vector may instead be of bacteriophage or a cosmid. If cloning occurs in mammalian cells, viruses also may be used as vectors.

If a plasmid is employed, it may be obtained from a natural source or artificially synthesized. Numerous plasmides especially adapted for replication of genes and/or high-level expression of proteins encoded by the genes, are widely commercially available. The particular plasmid chosen should be compatible with the contemplated transformation host, whether a bacteria such as *E. coli*, yeast, or other unicellular microorganism. The plasmid should include a proper origin of replication for the particular host cell to be employed.

Also, the plasmid should have a phenotypic property that will enable the transformed host cells to be readily identified and separated from cells that do not undergo transformation. Such phenotypic characteristics can include genes providing resistance to growth inhibiting substances, such as an antibiotic. Plasmids are widely commercially available that encode genes resistant to various antibiotics, including tetracycline, streptomycin, sulfa drugs, penicillin and ampicillin.

Transformation hosts for plasmid cloning vectors may include any appropriate prokaryotic or eukaryotic cell; however, preferably it is a welldefined bacteria, such as *E. coli*, or a yeast strain. Such hosts are readily rendered competent and capable of rapid growth in culture. Other forms of bacteria, such as Salmonella or pneumococcus, may be substituted for *E. coli*. In place of bacteria, other unicellular microorganisms may be used, for instance, fungi or algae. Whatever host is chosen, it should not contain or encode a restriction enzyme that would cleave the recombinant plasmid or a protease that will degenerate the expressed protein product.

In transformation protocols, typically only a limited portion of the host cells are actually transformed. The cells that have been transformed can be identified by placing the cell culture on agar plates containing a suitable growth medium and a phenotypic identifier, such as an antibiotic. Only those cells that have the proper resistance gene, e.g., to the antibiotic, will survive.

The identified transformed hosts are grouped into pools and plasmid DNA prepared from these pools is screened with a labeled probe, as discussed above. The pool(s) of clones that give a positive signal to the probe is identified and then the putative pool subdivided and the hybridization screen repeated. A single transformed positive colony corresponding to the GM-CSF gene is eventually identified. Plasmid DNA is prepared from the transformants and characterized by standard restriction enzyme analysis and by DNA sequencing, for instance, by standard chain-termination methods as originated by Sanger et al., *Proc. Natl. Acad. Sci.* (USA) 70:5463 (1977).

FIG. 1 depicts a partial restriction enzyme map of the human and murine GM-CSF genes and FIG. 2 illustrates the nucleotide sequences and the deduced amino acid sequences for murine and human GM-CSF gene and protein. The coding region of the human GM-CSF gene extends from nucleotide No. 52 to nucleotide No. 432. The coding region of the murine GM-CSF gene extends from nucleotide No. 10 to nucleotide No. 400. The corresponding amino acid sequences of human and murine GM-CSF, as determined from the nucleotide sequences, are set forth below and above the relevant human and murine codons, respectively. Plasmid DNA, designated as pHG 23 prepared from the human cDNA and transformed into *E. coli* is on deposit with the American Type Culture Collection ("ATCC"), 12301 Parklawn Drive, Rockville, MD 20852, USA, under Accession No. 39900.

It is to be understood that the GM-CSF gene can be "prepared" by techniques other than by the cloning methods mentioned above, set forth infra. For instance, the GM-CSF gene may be chemically synthesized as a single unit or in series of fragments that are subsequently ligated together to form the complete gene. Such techniques are commonly known to those skilled in the art to which the present invention is addressed. In addition, examples of such techniques are set forth in U.S. patent application No. 873,497, which is incorporated herein by reference, which patent application has been assigned to the same assignee as the present application.

Expression of Functional GM-CSF

Functional GM-CSF is produced by expressing the isolated GM-CSF gene in appropriate host cells, and then is tested for biological activity. In the expression procedure, cDNA fragments containing the coding region of the GM-CSF gene, for instance the human or murine GM-CSF genes shown in FIG. 2, are inserted into an appropriate, competent vector designed to direct expression of biologically active GM-CSF. As with the above-discussed cloning hosts, the transformation hosts for the expression vectors may include any appropriate prokaryotic or eukaryotic cells; however, preferably it is a welldefined bacteria such as *E. coli*, or a yeast strain. Such hosts are readily rendered competent and capable of rapid growth in culture. Applicants have discovered that the GM-CSF genes depicted in FIG. 2 are capable of high-level expression of biologically active GM-CSF in yeast hosts.

Figure 3:
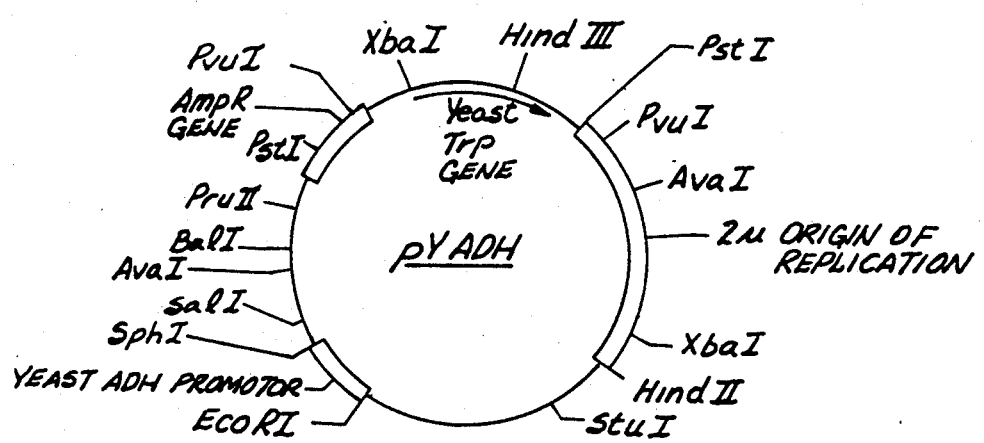
FIG. 3 illustrates the pYADH cloning vector.
Figure 4:
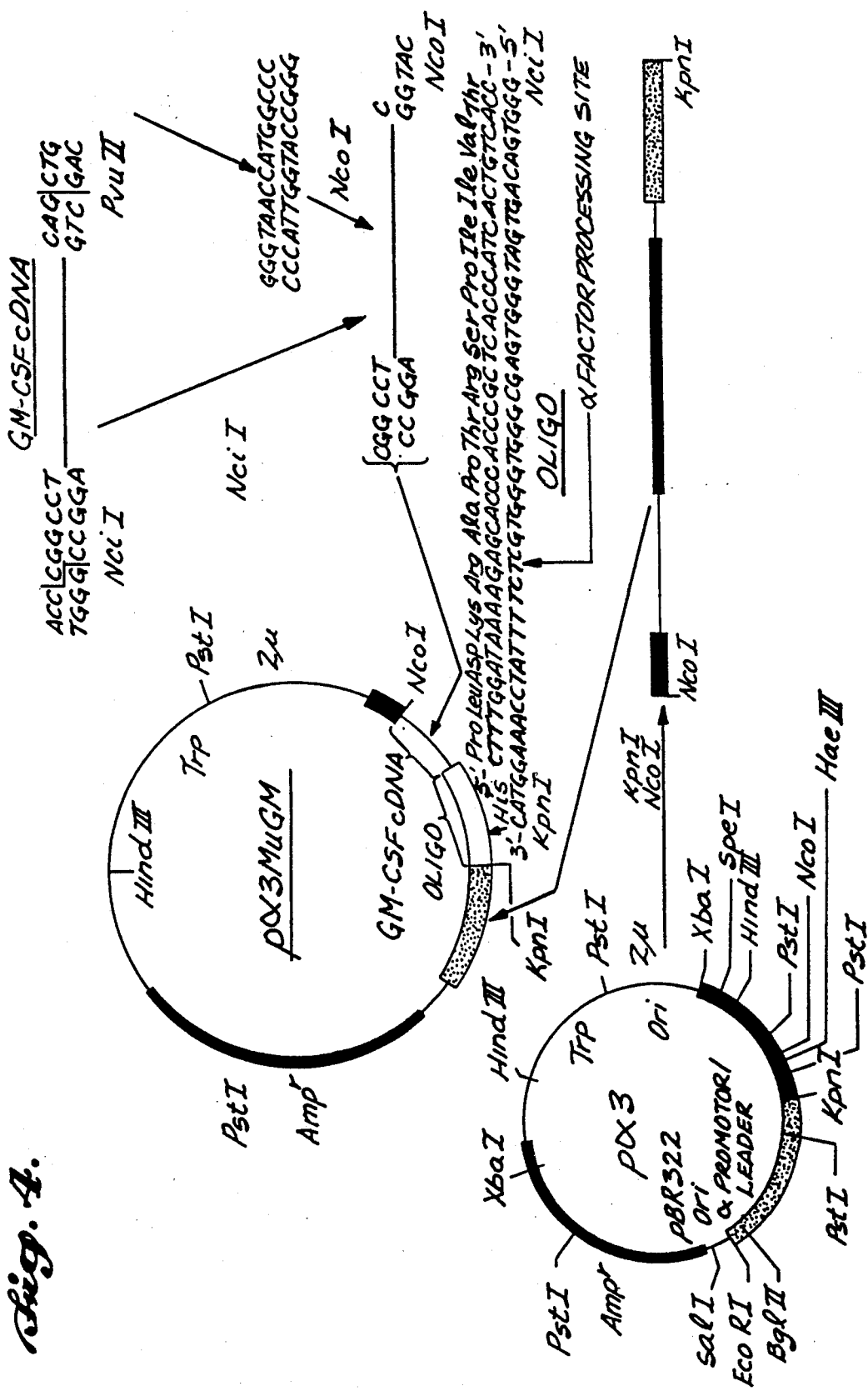
FIG. 4 illustrates the pα3 shuttle vector and the strategy employed for insertion of a murine GM-CSF cDNA into the shuttle vector.

In a preferred expression system of the present invention, the GM-CSF gene is inserted into a shuttle vector designed for replication of the gene and subsequent high-level expression of GM-CSF in yeast host cells. The shuttle vector preferably includes an origin of replication for the bacteria host and a phenotypic marker, such as an antibiotic resistance gene. Ideally, the shuttle vector also includes sequences from yeast, for instance, the tryptophan-1 gene (Trp-I) as a selectable marker and the 2 $\mu$ yeast origin of replication. Also, ideally, the shuttle vector includes a promoter together with leader sequences to direct high-level synthesis and secretion of the GM-CSF in yeast hosts. Promoters which have proven to be particularly useful in conjunction with the present invention include the alcohol dehydrogenase (ADH) promoter and the yeast pheromone $\alpha$-factor promoter. Ideally, the $\alpha$-factor leader sequence or other leader sequence is used in conjunction with the yeast promoter to direct secretion of the GM-CSF. Shuttle vectors meeting these criteria and having an ADH promoter (FIG. 3) or a pre-pro $\alpha$-factor promoter (FIG. 4) have been deposited with the ATCC under Accession Nos. 39967 and 53220, respectively.

The shuttle vector, with the GM-CSF gene inserted therein, is intially transformed into a bacteria strain, such as strain RR1 of *E. coli*, for replication of the gene. Standard techniques for carrying out such transformation are detailed in Maniatis et al., supra at 255; Bolivar et al., *Gene* 2:95 (1977); and, Peacock et al., *Biochem. Biophys. Acat.* 655:243 (1981). Other strains of *E. coli* which also could serve as suitable hosts include DH1 (ATCC No. 33849) and C600. The transformed *E. coli* hosts are selected with the phenotypic marker and then the recombinant plasmids containing the desired construct are identified by standard restriction enzyme analysis. Shuttle vectors that contain the GM-CSF gene in proper orientation are then transformed into an appropriate strain of *Saccharomyces cerevisiae* ("*S. cerevisiae*"). Preferable strains include, but are not limited to, 79, X2181-1B, DBY746, YNN282, and 20B-12. These strains are all α, Trp 1, Leu 2, for compatability with ADH /α-factor promoters and for selection of Trp+ transformants. These strains are widely available, for instance strain 79 is available from the Yeast Genetic Stock Center, Department of Biophysics and Medical Physics, University of California, Berkeley, Calif. 94720. Transformation of yeast hosts with a recombinant shuttle vector containing the GM-CSF gene may be conducted to well-known procedures, for instance as set forth in Beggs, *Nature* (London) 275:104 (1978); and, Hinnen et al., *Proc. Natl. Acad. Sci.* (USA) 75:1929 (1978).

Purification of Recombinant GM-CSF

The recombinant GM-CSF contained in the supernatant of the expression host cells is purified to essential homogeneity by reverse phase high-performance liquid chromatography ("HPLC"). The HPLC procedures used in the present invention preferably employ a reverse phase tetramethyl, octadecyl, octylmethyl or diphenyl-bonded silica column having a pore size sufficiently large to be optimally utilized with the protein GM-CSF, i.e., a pore size of at least 300 Å.

Suitable reverse phase HPLC columns for use in the practice of the present invention are articles of commerce. A preferable column for this purpose is the Vydac line of columns commercially available from Separations Group, Hesperia, CA. For example, the present invention may employ the Vydac C4 or C18 adsorbent reverse phase columns consisting of tetramethyl silane groups covalently bonded by means of siloxane (silican-oxygen-silican) bonded to the surface of 300 Å pore diameter silica gel which has been classified to a mean particle size of from 30 to 44 microns.

The elution of proteins from the HPLC column is carried out in a manner well known in the art. A suitable elution procedure for removing the bonded proteins from the column involves the use of a linear gradient of, for instance, acetonitrile in trifluoroacetic acid (TFA), or a linear gradient of N-propanol in pyridine-acetate buffer. The eluted protein can be conveniently monitored with detection systems that are well known in the art. For example, the relative protein concentrations in fractions eluted from the HPLC column can be determined by measuring absorbance of the eluted material in an automated ultraviolet light spectrophotometer, at 214 nanometers light wavelengths. A suitable automated ultraviolet light absorbance detection apparatus is available from Waters Associates, Milfred, MA.

Fractions recovered from the HPLC procedure are analyzed for protein by the fluorescamine assay and by sodium dodecyl sulfate polyacrylamide gel electrophoresis ("SDS-PAGE") followed by silver staining, as described by Laemmli, *Nature (London)* 227:680 (1970) and Oakley et al., *Anal. Biochem.* 105:361-364 (1980). The recovered GM-CSF is then assayed for biological activity using a bone marrow colony-forming assay, such as discussed above and in Examples A and B, infra.

If sufficient protein purification is not achieved by the initial HPLC procedure, it can be repeated by use of the same column or a different type of column. In addition, the same or a different eluant may be employed. By carrying out the HPLC in two steps, the GM-CSF was purified to homogeneity as a single symmetric peak of biological activity.

The processes and products of the present invention are further illustrated by the following alphabetically denominated examples of particular procedures used in the present invention and the subsequent illustrative examples which are numbered. The following examples are merely exemplary; they are presented to illustrate the present invention and to assist one of ordinary skill in making and using the same. The examples are not intended to limit in any way the scope of the disclosure of the claims set forth below or the protection granted by Letters Patent herein.

EXAMPLE A

Human Bone Marrow Colony Assay

This assay ascertained the capacity of the human GM-CSF to stimulate the formation of colonies of differentiated cells in semisolid cultures of bone marrow stem cells. Cells from the colonies that were generated were stained with orcein to visualize the types of cells present, i.e., granulocytes, macrophages, neutrophils, eosinophils, megakaryocytes, etc.

The assay employed a stock solution of nutrient medium and a stock agar composition. The agar is composed of 1.4 bacto-agar (Difco, Detroit, MI) in sterile distilled water. The stock nutrient medium, which may be stored for up to two weeks at 4° C., is of the following composition:
1. 28.5% (v/v) fetal bovine serum (FBS);
2. $0.7 \times 10^4$ Molar ("M") 2-mercaptoethanol;
3. 0.12 milligram per milliliter ("mg/ml") asparagine;
4. 0.7 mg/ml glutamine;
5. 150 units per milliliter ("U/ml") of penicillin G;
6. 150 U/ml of streptomycin;
7. $1.1 \times \alpha$-minimum essential medium (αMEM); and,
8. $2.2 \times$ vitamins (Gibco Laboratories, Chagrin Falls, OH), Cat #320–1120).

In the assay procedure, 50 microliter (ul) samples were plated in appropriate wells in log-2 dilution series. The agar for the bacto-agar solution, identified above, was prepared by placing the tube containing the agar suspension in a boiling water bath for approximately 10 minutes. Once the agar is in solution, it was transferred to a 40° C. bath.

The nutrient medium was warmed to 37° C., and then seven parts of the medium were mixed with three parts of the bacto-agar solution (hereinafter "incubation medium") and maintained at 37° C. Percoll treated bone marrow cells were then warmed to 37° C. and immediately added to the incubation medium at a final concentration of approximately $1 \times 10^5$ cells/ml. The bone marrow cell mixture was kept at 37° C. in the presence of 5% $CO_2$ while dispensing 250 ul aliquot into each well of the plate containing the samples to be tested. The plates were then swirled gently and allowed to sit at room temperature until the agar hardened. Thereafter the plates were placed in plastic boxes containing some distilled water to prevent the wells from drying out.

Colonies having 50 or more cells each were counted on days 7, 10 and 14. The earlier time was better for granulocyte colonies, and the latter time better for macrophage and mixed colonies. In each assay, several wells were plated without GM-CSF samples to obtain a background colony count. The average number of colonies that grew in the blank wells were subtracted from the number of colonies found in each of the wells containing the samples. The activity in colony forming units per milliliter ("CFU/ml") of the GM-CSF in the test samples was determined as being equal to the dilution of the sample at which the colony number is one-half of the maximum colonies formed by $1 \times 10^5$ bone marrow cells multiplied by the number of colonies observed in the half maximal case. In other words if a sample generated half maximal colonies (i.e., 35) at a dilution of 1:1000, that sample was said to contain $35 \times 1000$ or 35,000 CFU/ml.

The types of cells in the colonies were determined by picking the colonies and staining individual cells with a stain composed of 0.6% orcein and 60% acetic acid. In the staining procedure, an equal volume 50% methanol (MeOH) was added to each of the cultures and then the cultures were incubated at room temperature for 20 minutes. Thereafter, the 50% MeOH was aspirated off and then an equal volume of 100% MeOH was added to each culture, followed by incubation at room temperature for 20 minutes or overnight at 4° C. Next, the 100% MeOH was aspirated off and the culture dried.

The orcein stain mixture was added to the cell culture in an amount equal to 50% of the original volume of the culture. After approximately 20 minutes, the nuclei of the cells were visible. Thereafter, cultures were flooded with distilled water and then aspirated to remove the Orcein (which had precipitated). Next, distilled water in a volume equal to the original volume of a culture, was added which intensified the color of the stain and made it easier to evaluate the cell composition of the colonies.

EXAMPLE B

Murine Bone Marrow Colony Assay

The murine GM-CSF was analyzed in a murine colony forming assay employing the same materials and procedures as for the human colony forming assay in Example A above, except that in the murine assay the nutrient medium contained 20% horse serum, $5 \times 10^{-5}$M 2-mercaptoethanol, 84 micrograms per milliliter ("ug/ml") asparagine, 0.5 mg/ml glutamine, 150 U/ml penicillin, 150 U/ml streptomycin, $0.77 \times \alpha$MEM and $1.54 \times$ vitamins (Gibco). Also, the colonies are counted on days 4, 5 and 7.

EXAMPLE 1

In Vivo Therapeutic Studies

This investigation ascertained the ability of GM-CSF to prolong the life of and/or cause survival of mice which have been inoculated with a lethal dose of S. typhimurium. In a first study, A/J mice (Jackson Laboratories, Bar Harbor, ME) were given a lethal dose of S. typhimurium (20,000 organisms on day zero) by intraperitoneal injection. The infected mice were treated either with recombinant murine GM-CSF for 28 days at a dose of 5 ug/day or with mouse serum albumen (control group) at a dose of 5 ug/day. The recombinant GM-CSF and the mouse serum albumen were administered by intraperitoneal injection. As shown in FIG. 6, the control mice all died within 15 days. However, none of the mice treated with GM-CSF died until day 21, and 40% of such mice survived the S. typhimurium infection.

EXAMPLE 2

In Vivo Therapeutic Studies-Dose Response

A study similar to that set forth in Example 1 was conducted, but with much smaller doses of purified recombinant murine GM-CSF. In this particular study the A/J mice were inoculated by intraperitoneal injection with $1.75 \times 10^4$ S. typhimurium organisms. The animals were treated daily with intraperitoneal injections of purified recombinant murine GM-CSF at a dose of 0.3 ug/day. Control group mice were either not treated at all or treated daily with intraperitoneal injections of 3 ug of mouse serum albumen. As shown in FIG. 7, the control group mice all died within 30 days; however, mice treated with daily intraperitoneal injections of 0.3 ug of GM-CSF exhibited enhanced prolongation of life with 35% of such animals surviving the S. typhimurium infection. The results of this study and that set forth in Example 1 above, illustrate the efficacy of GM-CSF as an anti-infective therapeutic agent.

EXAMPLE 3

In Vivo Administration/In Vitro Colony Formation

The capacity of GM-CSF to function as an anti-infective agent was also investigated with in vitro studies. In one such study, A/J mice were given a lethal dose of $2 \times 10^4$ S. typhimurium organisms administered by intraperitoneal injection. Several mice were treated daily with intraperitoneal injections of 5 ug of purified, recombinant GM-CSF. Other such infected mice were given daily intraperitoneal injections of 5 ug of murine serum albumen. Replicate groups of treated and untreated animals were sacrificed on days 2, 3, 4, and 7. The spleens and livers of the sacrificed animals were harvested and single cell suspensions were prepared by grinding the spleens and livers in phosphate buffered saline ("PBS") and sand with a mortar and pestle. Dilutions of the resulting homogenate were plated on SS agar (Difco) and incubated overnight at 37° C. The SS agar permits the selective growth of Salmonella and Shigella organisms. Salmonella colonies were counted on the following day. Single cell suspensions of peritoneal wash from the harvested animals also were prepared, with such cells likewise being plated on SS agar.

As shown in FIG. 8, the animals which were treated with GM-CSF possessed significantly fewer S. typhimurium microorganisms in the various organs, i.e., peritoneal cavity, spleen and liver, than did the mice which received an identical dosage of control protein, i.e., mouse serum albumen.

EXAMPLE 4

Dose Dependent In Vivo Administration/In Vitro Colony Formation

A study similar to that detailed in Example 3 was conducted by treating mice infected with S. typhimurium with various doses of purified recombinant murine GM-CSF and then ascertaining the levels of infection present in the spleens of treated and untreated animals. In this particular study the mice were infected with $2 \times 10^4$ S. typhimurium organisms by intraperitoneal injection. Different groups of such mice were treated on days 0, 1, 2, and 3 with doses of 0.01 ug, 0.1 ug, 1 and 10 ug per dose of GM-CSF. Also, a control group of the infected mice were untreated. On the third day the animals were sacrificed and their spleens harvested.

Single cell suspensions of spleen cells were prepared as set forth above in Example 3, with the cells being plated on SS agar to ascertain the number of *S. typhimurium* colonies resulting.

As shown in the table set forth in FIG. 9, animals treated with the recombinant murine GM-CSF at each of the administered dosages exhibited a significant decline in the number of *S. typhimurium* organisms which populated the spleen relative to those animals which were untreated. The results of this particular study and that set forth in Example 3, further verify the efficacy of GM-CSF as an anti-infective therapeutic agent. Also, this particular study indicates that dosages in the full range of 0.01 ug to 10 ug of GM-CSF per 20 g mouse were found to be effective. This corresponds to dosages of 0.05 to 500 ug per kg of body weight.

EXAMPLE 5

Preparation of Recombinant Murine GM-CSF

LBRM-33-5A4 cells at a concentration of approximately $2 \times 10^6$ cells per ml were cultured in 100–500 ml volumes in Roswell Park Memorial Institute ("RPMI")-1640 medium supplemented with 10% (v/v) fetal calf serum ("FCS"), 2 millimolar ("mM") glutamine, 100 U/ml penicillin and 100 ug/ml streptomycin. The LBRM-33-5A4 cell line is on deposit with the ATCC under Accession No. ATCC-CRL-8080. The cells were cultured in the presence of 1% PHA for about 12 hours in a humidified atmosphere of 5% $CO_2$ in air. After this period of time, viable cells were harvested by centrifugation.

Total RNA was extracted from the LBRM-33-5A4 cells by the standard method described by Chirgwin et al., supra. In this procedure guanidinium thiocyanate was used to denature the cellular protein including the RNase at a rate that exceeds the rate of RNA hydrolysis by RNase. The mRNA was removed from the cellular protein by ultracentrifugation through a dense cushion of cesium chloride.

Thereafter, polyadenylated mRNA was separated from the total RNA on an oligo (dT)-cellulose chromatography column using the standard method disclosed by Maniatis et al., supra at 197. Briefly, the column was prepared with application buffer (20 mM Tris-Cl (pH 7.6), 0.5M NaCl, 1 mM ethylene diamine tetra acetate (EDTA) and 0.1% sodium dodecyl sulfate (SDS). The RNA, in application buffer, was loaded onto the column. The nonadsorbed material was removed from the column by initial washings with application buffer followed by additional washings with application buffer containing 0.1M NaCl. The retained polyadenylated mRNA was eluted with buffers of reduced ionic strength composed of 10 mM Tris-Cl (pH 7.5), 1 mM EDTA and 0.05% SDS. The eluted polyadenylated mRNA was precipitated at $-20°$ C. with 1/10 volume sodium acetate (3M, pH 5.2) and 2.2 volumes of ethanol. After elution of the polyadenylated mRNA from the oligo (dT)-cellulose column, the integrity of the polyadenylated mRNA was confirmed by electrophoresis through agarose gels, by the standard method set forth in Maniatis et al., supra at 199.

A library of double-stranded cDNA corresponding to the mRNA was prepared from the purified, polyadenylated mRNA by employing the standard procedure detailed by Maniatis et al., supra at 229. Oligo-dT was hybridized to the polyadenylated tail of the mRNA to serve as the primer for the reverse transcription of the first cDNA strand. The enzyme AMV reverse transcriptase synthesized the first DNA strand by using the mRNA as a template. This procedure resulted in a hairpin loop being formed at the 3' end of the initial cDNA strand that serves as an integral primer for the second cDNA strand. After the mRNA strand has been degraded with NaOH, the second cDNA strand was synthesized with DNA polymerase I. The hairpin was then removed with nuclease S1 to produce double-stranded cDNA molecules.

The double-stranded cDNA was fractionated into size classes by Sephacryl S-400 (Pharmacia Fine Chemicals, Piscataway, N.J.) column chromatography and monitored by analysis using alkaline agarose electrophoresis employing end-labeled fragments of pBR322 DNA as molecular-weight markers. cDNA having a length of less than 500 base pair (bp) was discarded to avoid needless cloning of these undersized cDNA fractions.

The double-stranded cDNA fractions, as prepared above, were inserted into the Pst I site of the pBR322 plasmid by the standard method contained in Maniatis et al., supra, beginning at 239. In this procedure, the double-stranded cDNA was tailed with poly (dC) at its 3' ends. The plasmid pBR322 (Pharmacia Fine Chemicals) was digested with Pst I endonuclease and then tailed with poly (dG) at its 3' ends. The tailed plasmid DNA and the tailed cDNA were annealed in annealing buffer (0.1M NaCl, 10 mM Tris-Cl (pH 7.8) and 10 mM ETDA) to form recombinant plasmids. All restriction enzymes described herein are commercially available from New England Biolabs, Beverly, MA.

The recombinant plasmids were transformed into *E. coli* strain MM294 by using the standard procedure of Hanahan, *J. Mol. Biol.* 166:557 (1983), in which the *E. coli* cells were prepared by growth in elevated levels of $Mg^{2+}$. The transformation hosts were plated and then transformants were identified by use of tetracycline as a phenotypic identifier. By this technique, applicants obtained approximately $6 \times 10^4$ independent transformants.

A synthetic oligonucleotide probe was chemically synthesized by standard triester method, as detailed by Sood et al., *Nucl. Acid Res.* 4:2557 (1977); and, Hirose et al., *Tet. Lett.* 28:2449 (1978), and then radiolabeled with $^{32}P$ for use in screening the murine cDNA library. The probe was composed of the following nucleotide sequence: 5'-TGATGGCCTCTACATGCTT-CCAAGGCCGGTAACAATTAT-3'. This probe complements the 5' terminal portion of the sense strand of the published sequence of the gene coding for murine GM-CSF, Cantrell et al., supra. It has the advantage of being short enought to be relatively easily synthesized, while being long enough to contain sufficient information to be useful as a probe for the murine GM-CSF gene. It is to be understood, however, that the composition of the probe may correspond to other portions of the murine GM-CSF gene without departing from the scope or spirit of the present invention. To facilitate labeling, the 5' ends of the oligonucleotides are synthesized with OH termini, thereby eliminating the phosphatase treatment which typically must be employed when labeling DNA fragments. The labeling protocol included adding 1 ul of the synthetic oligonucleotides to 16 ul of $^{32}P$-ATP (7000 Ci/mM), 1 ul (10 U) of T4 polynucleotide kinase and 2 ul of $10 \times$ kinase buffer I (0.5M Tris-Cl (pH 7.6), 0.1 $MgCl_2$, 50 mM dithiothreitol, 1 mM spermidine and 1 mM ETDA). The reaction was carried out at 37° C. for thirty minutes, and thereafter the synthesized oligonucleotides were extracted with phenol/chloroform. The labeled probes were separated from unlabeled oligonucleotides by chromatography on Sephadex G-50 columns (Pharmacia Fine Chemicals).

To facilitate initial screening of the murine cDNA library, the transformed bacterial cultures were grouped into pools, each having approximately 3000 different clones. Plasmid DNA was removed from samples of the host bacteria by standard alkaline lysis method detailed by Ish-Horowicz and Burke, *Nucl. Acids Res.* 9: 2989 (1981). The isolated plasmids were digested to completion with Pvu II and Hind III by standard procedures. Next, the plasmid digests were fractionated by electrophoresis through 0.8% agarose gel and then blotted onto nitrocellulose filter by the standard method of Southern, *J. Mol. Biol.* 98:503 (1975). After the transfer process, the filter was air-dried and baked for two hours at approximately 80° C. under a vacuum to bind the DNA fragments to the nitrocellulose.

The bound DNA was next hybridized with the labeled cDNA probe. Briefly, the baked nitrocellulose was incubated at 55° C. for 2-4 hours in prehybridization buffer composed of: 6×SSC; 0.5% NP40 detergent; 0.1% sarcosyl; 5×Denhardt's solution (0.02% Ficoll, 0.02% polyvinylpyrrolidone, 0.02% "bovine serum albumen"); and, 100 ug/ml denatured salmon sperm DNA (Sigma Type-III sodium salt). The filter was then incubated overnight at 55° C. with the $^{32}$P-labeled cDNA probe ($10^6$ CPM/ml) in hybridizing solution as above. After overnight hybridization, the filter was washed extensively with 6×SSC at room temperature and then for 1 hour at 42° C. and then for 1.5 hours at 55° C. with 6×SSC. After air drying, the filter was subjected to autoradiography at −70° C.

From the autoradiography, applicants found a number of strongly hybridizing bands. One putative pool of clones from which the plasmid DNA that produced a strongly hybridizing band was obtained, was subdivided into pools of approximately 500 transformants and the hybridization screening procedure repeated. The putative subpool from which a strongly hybridizing band of DNA was seen was then plated. The resulting colonies were probed with the radiolabeled cDNA nucleotide probe by the well-known methods of Grunstein and Hogness, *Proc. Natl. Acad. Sci.* (USA) 72:3961 (1975), using the hybridizing conditions described above. By this process, a single positive host colony was identified.

cDNA was prepared from the plasmid DNA removed from the positive colony and analyzed by standard restriction enzyme analysis. A portion restriction enzyme map of the murine GM-CSF gene is illustrated in FIG. 1. The prepared cDNA also was sequenced by the standard chain-termination method as originated by Sanger et al., supra. The details of this method are set forth in U.S. Pat. No. 4,322,499 and in the Amersham Handbook entitled, *M13C Cloning And Sequencing*, Blenheim Crescent, London (1983) (hereinafter "Amersham Handbook"). The nucleic acid sequence of the murine cDNA is illustrated in FIG. 2. The coding region of the murine GM-CSF gene extends from nucleotide No. 10 (Ala residue) to nucleotide No. 400 (Lys residue). The corresponding amino acids, as determined by the nucleic acid sequence, are set forth above the corresponding codons.

Substantially the entire coding region and a portion of the 3' flanking region of the GM-CSF gene was removed from the murine cDNA clone and inserted into the pMLSVN1/N4-S plasmid at the Pst I restriction site. The pMLSVN1/N4-S plasmid has been deposited with the ATCC under accession No. 39890. The GM-CSF cDNA was then excised from the pMLSVN1/N4-S plasmid to provide an insert which could be placed into the Pα3 based shuttle vector, as detailed in FIG. 4. The resulting expression plasmid containing the murine GM-CSF cDNA is designated as Pα3 MuGM.

To form the Pα3 MuGM plasmid the coding region of the GM-CSF gene from the Nci I to the Pvu II site in the flanking region of the pMLSV-N1/N4-S plasmid was removed by use of Nci I and Pvu II restriction enzymes in a standard protocol, for instance as set forth in Maniatis et al. supra. The resulting DNA fragment was treated with T4 DNA polymerase to remove the 5' overhang at the Pvu II terminal. Nco I linkers were added to the 3' end of the isolated cDNA by standard procedures, for instance, as set forth in Maniatis et al., supra, to enable the cDNA fragment to be ligated to the Nco I site in the Pα3 shuttle vector. The Nco I linkers of the composition: GGGTAACCATGGCCC, include the stop codon on TAA. The Nco I linkers were digested with Nco I restriction enzyme to generate a cohesive 3' end. The resulting Nci I-Nco I cDNA fragment was purified by electrophoresis through agarose gel.

The Nci I enzyme cleaved the GM-CSF gene from the cDNA clone at a location which is ten nucleotides downstream from the 5' terminus of the coding region for the mature protein since no restriction site was found to correspond precisely to the 5' terminus. An oligonucleotide was chemically synthesized to add back a 5' terminal portion of the coding region of the mature GM-CSF gene and also to provide the α-factor leader sequence to direct secretion of the heterologous protein in yeast host cells. The composition of the oligonucleotide (shown in Table 1 below, and in FIG. 4 (open box portion)), includes a Kpn I cohesive 5' terminal followed by the α-factor leader sequences and then by the amino-terminal ten amino acids of the GM-CSF gene to terminate at a 3' Nci I site. Although the oligonucleotide shown in Table 1 was chemically synthesized by triester technique as detailed by Sood et.al., supra; and, Hirose et.al., supra, it is to be understood that the oligonucleotide can be prepared by other methods, such as by phosphodiester method.

TABLE 1

| (Kpn I) | 5' | CT | TTG | GAT | AAA | AGA | GCA | CCC | ACC | CGC | |
|---|---|---|---|---|---|---|---|---|---|---|---|
| | 3' | CAT | GGA | AAC | CTA | TTT | TCT | CGT | GGG | TGG | GCG |
| | | His | Pro | Leu | Asp | Lys | Arg | Ala | Pro | Thr | Arg |
| | | TCA | CCC | ATC | ACT | GTC | ACC | 3' | | (Nci I) | |
| | | AGT | GGG | TAG | TGA | CAG | TGG | G | 5' | | |
| | | Ser | Pro | Ile | Thr | Val | Thr | | | | |

To form the Pα3MuGM plasmid, a 3-way ligation was performed with the Nco I-Kpn I digested Pα3 plasmid, the Kpn I-Nci I linking oligonucleotide (Table 1), and the Nci I-Nco I cDNA fragment. In the ligation procedure, approximately 50 nanograms (ng) of the vector fragment was ligated together with approximately 10 ng of the linker oligonucleotide and 25 ng of the GM-CSF cDNA. Next, the ligation mixture was transformed into *E. coli* strain RR1 using standard transformation techniques, for instance, as set forth in Bolivar et al., supra; and, Peacock et al., supra. This strain of *E. coli* is widely commercially available. The host cells were grown in culture, removed from the culture and then lysed. Plasmids from the host cells that were transformed were checked for correct orientation of the GM-CSF gene fragment and the linking oligonucleotide within the plasmid by standard restriction enzyme analysis, for instance using the techinques dicussed by Maniatis et al., supra at 374, and by Smith and Birnstiel, *Nucl. Acid Res.* 3:2387 (1976).

After confirming that the DNA fragments were ligated in proper relative location, the recombinant DNA shuttle vector Pα3MuGM, was then transformed into yeast strain 79 (α, Trp 1-1, Leu 2-1) of *S. cerevisiae* for selection of Trp+ transformants by standard techniques. Prior to transformation, the strain 79 was grown in culture in YPD medium (1% [wt/vol] Yeast Extract, 2% [wt/vol] Peptone, 2% [wt/vol] glucose supplemented with 80 ng/ml adenine and 80 ng/ml uracil), to a density of $2 \times 10^7$ cells/ml. Cells were harvested by centrifugation at $1000 \times g$ for 5 minutes at 22° C., and then the resulting pellet was washed with sterile, distilled water.

The yeast cells were then concentrated by resuspending in 1/10 vol. of SED (1M sorbitol, 25 mM EDTA [pH 8.0], and 50 mM dithiothreitol) and incubating for 10 minutes at 30° C. The cell-buffer mixture was then centrifuged for 5 minutes at $300 \times g$. The pellet was washed once with 1/10 vol. of 1M sorbitol and the cells resuspended in 1/10 volume of SCE (1M sorbitol, 0.1M sodium citrate [pH 5.8], 0.01M EDTA). Glusulase, to break down the cell walls, in an amount of $10^{-3}$ vol., was added to the solution and then the solution incubated at 30° C. for 30 minutes with occasional gentle shaking. The presence of spheroplasts was assayed by diluting 10 ul of the yeast cells into a drop of 5% SDS (wt/vol) on a microscope slide to observe for "ghosts" at $400 \times$ phase contrast. The cell mixture was then centrifuged at $300 \times g$ for 3 minutes. The resulting pellet was twice washed with 1/10 vol. of 1M sorbitol. The pellet was then once washed with CaS (1M sorbitol, 10 mM CaCl$_2$).

The yeast spheroplasts were then transformed with the previously prepared expression vector in a procedure adapted from Beggs, supra. The pelleted spheroplasts were suspended in 1/200 vol. of CaS and then divided into 100 ul aliquots in 1.5 ml Eppendorf tubes. Then, from 1 to 10 ul of the plasmid DNA were added to each aliquot (0.5 to 5 ug). The mixture was incubated at room temperature for 15 minutes and then 1 ml of polyethylene glycol ("PEG") (20% PEG 4000, 10 mM CaCL$_2$, 10 mM Tris-HCl [pH 7.4]) was added to each aliquot to promote DNA uptake. After 15 minutes at room temperature, the mixture was centrifuged for 5 minutes at $350 \times g$. The resulting pellet was resuspended in 150 ul of SOS (10 ml of 2M sorbitol, 6.7 ml of YPD medium, 0.13 ml of 1M CaCl$_2$, 27 ul of 1% tryptophan and 3.7 ml of water). This mixture was incubated for 20 minutes at 30° C. The cells were then plated.

Prior to plating the protoplast/DNA mixture, selective plates were preincubated at 37° C. three ml of melted top agar (45° C.), composed of: 18.2 ml of sorbitol; 2 gm agar; 0.6 gm Difco yeast nitrogen base (without amino acids); 2 gm glucose; 0.1 ml of 1% adenine; 0.4 ml of 1% uracil; and, amino acids as required, was then added to each aliquot of transformed cells and the tube contents poured on the selective plates. The plates were incubated from 2 to 4 days at 30° C. Colonies which developed in the Trp minus medium contained plasmids that have the Trp 1 gene, i.e., those that were transformed.

Prior to biological assay, the transformants were grown in 20-50 ml of YPD medium at 30° C. to stationary phase. At the time of harvest, the protease inhibitors phenyl methyl sulfonyl ("PMSF") and Pepstatin A were added to final concentrations of 1 mM and 10 uM, respectively. The cells were then removed by centrifugation at $400 \times g$ and the medium was filtered through a 0.45 micron cellulose acetate filter (Corning Glass Works, Corning, N.Y.). The sterile supernates were stored at 4° C. The resulting supernates, as assayed with the colony forming assay of Example B, contained approximately $2 \times 10^5$ GM-CSF CFU/ml or 5 ug of recombinant GM-CSF per ml of yeast fermentation fluid.

Larger scale fermentations were carried out in a 10 liter New Brunswick Microferm fermentor. Cells were removed from the medium using a Millipore Pellicon filtration system. The filtered medium was purified by multiple HPLC procedures with a Waters LC 500 A preparative chromatograph equipped with a Waters Prep LC gradient generator. To this end, the filtered medium was pumped directly onto a Waters Prep PAK cartridge packed with Vydac C 4, 15 u reverse phase silica packing at a flow rate of 100 ml/min and at a pressure of 10 atmospheres. Up to 20 liters of medium were applied to the column at one time. The loaded column was washed with 0.1% TFA in water to remove nonbound components until absorbance at an optical density of 280 nm, as monitored with an LKB 2238 Uvicord II absorbance detector (LKB Instruments, Inc.), dropped to baseline (preloading) values. Elution of the bound protein was accomplished with a linear gradient of 0-95% acetonitrile in 0.1% TFA (v/v) (pH 2.0-2.1) at a rate of 2% acetonitrile per minute. One minute fractions were collected and analyzed by SDS PAGE. Peak protein fractions were observed in fraction Nos. 27 and 28.

The peak fractions containing recombinant GM-CSF from the first HPLC procedure were collected and then diluted 1:1 (v:v) in 0.1% TFA and then applied to the same Prep PAK column used above which had been previously equilibrated in 0.1% TFA and 25% acetonitrile. Elution of the bound protein was carried out with a linear gradient of 25-100% acetonitrile applied to the column at the rate of 1% acetonitrile per minute and at a flow rate of 100 ml/min. One minute fractions were collected.

The collected fractions were analyzed for protein by a fluorescamine assay and also by SDS PAGE followed by silver staining. In the electrophoresis process, 20 ul aliquots from the fractions collected during the elution procedure were dried under vacuum after the addition of 2 ml of 10% SDS to each aliquot. The dried residue was dissolved in 40 ul of reducing sample buffer composed of 0.0625M Tris (pH 6.8); 2% SDS (w/u); 10% glycerol (v/v); and 5% 2-mercaptoethanol (v/v). The solution was boiled for 3 min. and then subjected to electrophoresis on 12% polyacrymide gel by the method described by Laemmli, supra. The gel samples for the individual fraction numbers were silver stained by the method described by Oakley et al., supra. Essential homogeneity of the recombinant murine GM-CSF was confirmed by the electrophoresis and silver staining. This homogenous material exhibited a specific activity of approximately $3 \times 10^5$ CFU/ug of protein.

EXAMPLE 6

Preparation of Recombinant Human GM-CSF

Recombinant human GM-CSF was prepared using essentially the same method discussed above in Example 5 relative to murine GM-CSF. The human GM-CSF was prepared from cell lines thought to produce relatively high levels of lymphokines under the assumption that they might also produce human GM-CSF. These sources included malignant cell lines such as a human lymphoma T-call line. Applicants have prepared cDNA libraries from several human lymphoma T-cell lines, such as HUT-102 and Jurkat. These particular cell lines are available from a wide variety of sources and have been used extensively by researchers. For example, HUT-102 cells were cultured in a concentration of approximately $2 \times 10^6$ cells/ml in 100-500 ml volumes of RPMI-1640 medium supplemented with 10% (v/v) FCS, 2 mM glutamine, 100 U/ml penicillin and 10 ug/ml streptomycin. The cells were cultured for approximately 3-5 days in a humidified atmosphere 5% $Co_2$ in air. After this period of time, viable cells were harvested by centifugation. As in the procedure for murine GM-CSF, discussed above, total RNA was extracted from the HUT-102 cells by the standard method described by Chirgwin et al., supra and then polyadenylated mRNA prepared from the extracted total RNA.

GM-CSF also was prepared from activated human peripheral blood mononuclear cells. For use in the present invention, the peripheral blood T-lymphocyte cells (mixture from Portland, Oreg. Red Cross) at a concentration of approximately $2 \times 10^6$ cells/ml were cultured in 100-500 ml volumes in RPMI-1640 medium supplemented with 10% (v/v) FCS, 2 mM glutamine, 10 U/ml penicillin and 100 ug/ml streptomycin, together with 20 ug/ml concanavalin A (Con A) (Pharmacia Fine Chemicals), and 10 ng/ml phorbol myristate acetate (PMA) Sigma Chemcial Company, St. Louis, MO). The cells were cultured for approximately 20 hours in a humidfied atmosphere 5% $CO_2$ in air. After this period of time, viable cells were harvested by centrifugation. Thereafter, total RNA was extracted from the peripheral blood T-cells and polyadenylated mRNA prepared from the extracted total RNA as described above in Example 5.

A library of double-stranded cDNA corresponding to the mRNA was prepared from the purified polyadenylated mRNA of the HUT-102 cells and of the peripheral blood T-lymphocyte cells using the standard procedures discussed above in Example 5 and detail by Maniatis et al., supra. The double-stranded cDNA from the HUT-102 cells and from the peripheral blood T-lymphocyte cells were cloned by insertion into the pBR322 plasmid which was then used to transform E. coli strain MM294, supra, in Example 5. The transformation hosts were plated and then transformants were identified by use of a phenotypic identifier. By this technique, approximately $2 \times 10^6$ independent transformants were obtained. These transformants were grouped into pools each having approximately 100,000 different clones. Plasmid DNA was prepared from samples of the host bacteria using the procedure discussed above in Example 5 and then screened with a labeled cDNA probe composed of 372 bp fragment of the murine GM-CSF cDNA clone identified by the underlining in FIG. 2 (nucleotide No. 43 to nucleotide No. 414). For use as the probe, the murine cDNA was radiolabeled by nick translation by the standard procedure set forth in Maniatis et al., supra at 108. By this process, the probe was labeled to a specific activity of approximately $5 \times 10^8$ CPM/ug DNA. The resulting labeled probe was used to screen the human cDNA library using the same techniques as set forth above in Example 5. From the screening process, a single positive host colony was identified. Plasmid designated as pHG23 was prepared with cDNA from the identifed positive colony. The plasmid cDNA was analyzed by standard restriction enzyme mapping (FIG. 1) and sequenced by the standard chaintermination protocol as described in the Amersham Handbook, supra (FIG. 2). Samples of the host plasmid transformed into E. coli are on deposit with the ATCC under Accession No. 39900.

Figure 5:
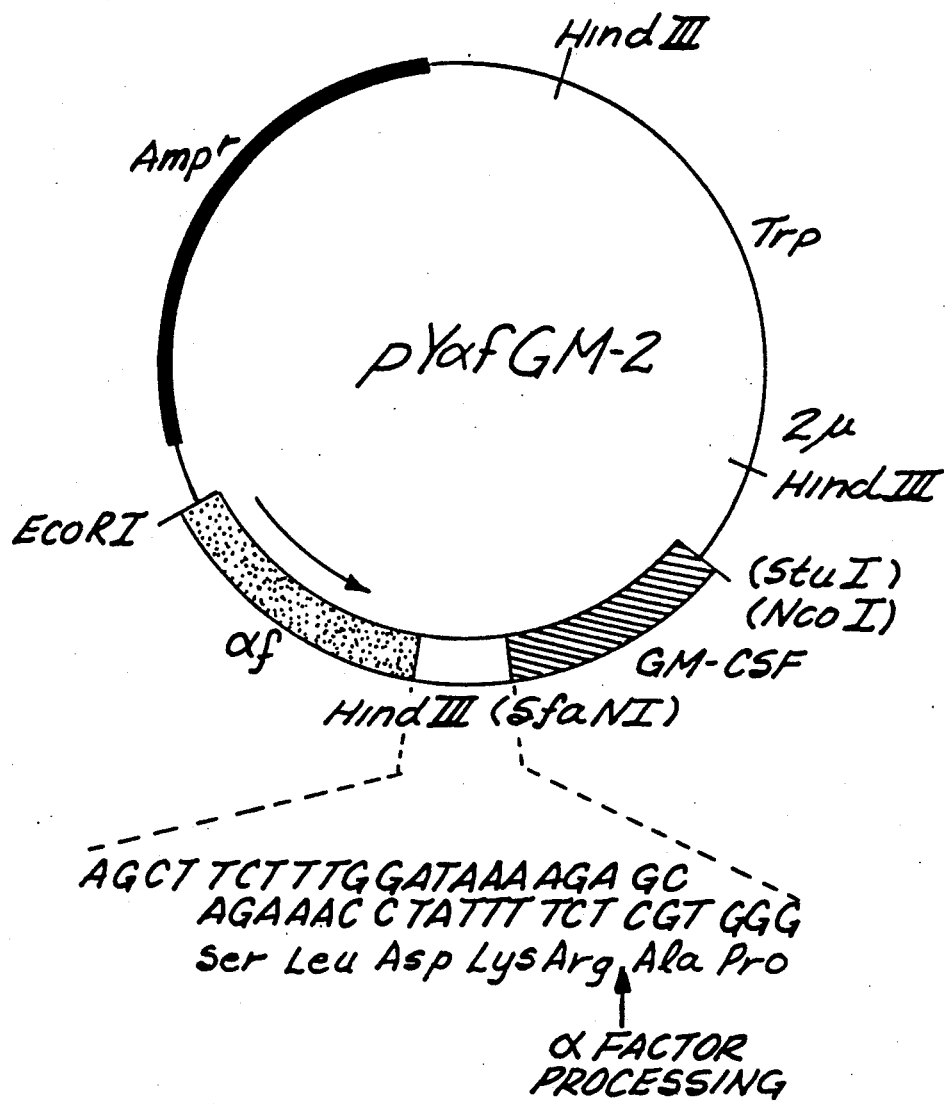
FIG. 5 illustrates the pYαfGM-2 shuttle vector used to clone the human GM-CSF gene in a bacteria host and to express functional GM-CSF in a yeast host.

The pHG23 clone was employed to express mature human GM-CSF. To this end, substantially the entire coding region and a portion of the 3' flanking region of the human GM-CSF gene was removed from the cDNA clone and inserted into plasmid p 3 with a linking oligonucleotide to form a shuttle vector, designated as pY fGM-2, to direct high-level GM-CSF expression in yeast host cells. The pY fGM-2 expression plasmid, as shown in FIG. 5, is on deposit with the ATCC under Accession No. 53157.

To form the shuttle vector, substantially the entire coding region of a GM-CSF gene, from the SfaN I to the Nco I site, was removed from the pHG23 clones by use of SfaN I and Nco I restriction enzymes in a standard protocol, for instance as set forth in Maniatis et al., supra at 104. The GM-CSF gene segment was cleaved from the pHG23 clone at the SfaN I site, which is located two nucleotides downstream from the 5' terminus of the region coding for the mature protein (nucleotide No. 53 in FIG. 2), since no restriction site was found to correspond precisely to nucleotide No. 51. An oligonucleotide was chemically synthesized to add back the 5' terminal portion of the coding region of the mature GM-CSF gene and also to add the α-factor processing site so as to obtain complete processing of the signal for secretion of the mature form of GM-CSF. The composition of the oligonucleotide, as shown in Table 2 below, and in FIG. 5, includes a Hind III cohesive 5' terminal, followed by a cathepsin B-like maturation site composed of the sequence: TCT TTG GAT AAA AGA, and a Sfa NI cohesive 3' terminus encoding the first two amino acid residues of the mature GM-CSF protein. Although the oligonucleotide shown in Table 2 was chemically synthesized by triester technique as detailed by Sood et al., supra and Hirose et al., supra, it will be appreciated that the oligonucleotide can be prepared by other methods, such as by the phosphodiester method.

TABLE 2

```
5' A GCT TCT TTG GAT AAA AGA GC     3'
3'   AGA AAC CTA TTT TCT CGT GGG   -5
     Ser Leu Asp Lys Arg Ala Pro
```

It is to be understood that other standard recombinant DNA techniques could be used to generate the same expression vector, and that the construction methods detailed above are merely representative of various strategies that could be used to prepare a GM-CSF cDNA fragment for insertion into the pYαfGM-2 expression vector.

The pYαfGM-2 plasmid was used to transform yeast strain 79 in the same manner discussed above in Example 5. The resulting human GM-CSF was filtered and purified to homogeneity by multiple HPLC procedures. To this end the filtered medium was pumped with a Milton Roy pump (LAB Data Control, Riveria Beach, FL) at a flow rate of 5 ml/min directly onto a Vydac C4 reversed phase column (1.0×30 cm stainless steel with 10 u packing or Waters radial compression cartridge [Waters Associate] custom packed with 15 u Vydac C4 packing. Several liters of medium were applied at a time. The loaded column was washed with 0.1% TFA to remove nonbound components until the opical absorbance at 214 nm as monitored with a LKB 2238 Uvicord II spectrophotometer, dropped to baseline (preloading) values. Elution of the bound protein was accomplished with a linear gradient of 0-95% acetonitrile in 0.1% TFA (v/v) (pH 2.0-2.1) at a rate of 1% acetonitrile/min. The gradient was formed with a Waters liquid chromatograph consisting of a Model 680 gradient former, 2 M-45 pumps and a Model 414 detector monitoring at 214 nm. Peak protein fractions were observed at from 55 to 60% acetonitrile.

The peak fractions containing recombinant GM-CSF from the first HPLC procedure were collected and then diluted 1:3 in 0.1% TFA (v/v) in $H_2O$, and then the activity was subjected to re-chromatography and re-elution with the same gradient of TFA and acetonitrile on a Vydac C18 column (3.9 mm×15 cm column, 5 u packing). Peak fractions were observed at from 55 to 60% acetonitrile.

Fractions were analyzed for protein by fluorescamine assay. Also, essential homogeneity of the recombinant human GM-CSF was confirmed by the electrophoresis and silver staining procedures discussed in Example 5. The activity of this homogeneous material, as analyzed with the colony forming assay detailed in Example A above, was found to be approximately $1.5 \times 10^7$ CFU/ml, with a specific activity of approximately $1.5 \times 10^6$ CFU/ug of protein. The pI value was found to be approximately from 5.0 to 5.5.

While the present invention has been described in conjunction with preferred embodiments and illustrative examples, one of ordinary skill after reading the foregoing specification will be able to effect various changes, substitutions of equivalents, and other alterations to the methods and compositions set forth herein. It is therefore intended that the protection granted by Letters Patent hereon be limited only by the appended claims and equivalents thereof.

The embodiments of the invention in which an exclusive property or privilege is claimed are defined as follows:

1. A method of treating infectious bacterial diseases, comprising the step of introducing into a mammalian subject in need of treatment, a therapeutically effective amount of granulocyte-macrophage colony stimulating factor (GM-CSF).

2. The method of claim 1, wherein the GM-CSF is of recombinant origin.

3. The method of claim 1, wherein the GM-CSF is purified to a specific activity of from about $6 \times 10^4$ to $1.5 \times 10^6$ colony forming units per microgram of protein as determined by bone marrow colony forming assay.

4. The method of claim 1, wherein the GM-CSF is introduced into the body by injection.

5. The method according to claim 4, wherein the method of injection is selected from the group consisting of subcutaneous, intramuscular, intraperitoneal and intravenous injection.

6. The method of claim 1, wherein the GM-CSF is introduced by a method selected from the group consisting of aerosol inhalation, transdermal or transbuccal absorption and rectal suppository.

7. The method of claim 1, wherein the dosage of GM-CSF introduced into the body is approximately 0.05 ug to 500 ug per kilogram of body weight.

8. The method of claim 1, wherein the doses of GM-CSF are periodically introduced into the body.

9. A method of killing bacterial microorganisms in vivo in an animal by introducing into the animal an effective dosage of GM-CSF.

10. The method of claim 9, wherein the GM-CSF consists essentially of purified recombinant GM-CSF.

11. The method of claim 10, wherein the GM-CSF is introduced into the animal by a method selected from the group consisting of injection, aerosol inhalation, transdermal or transbuccal absorption and rectal suppository.

12. The method of claim 10, wherein the GM-CSF is introduced into the animal at a dosage of from approximately 0.05 ug to 500 ug per kilogram of animal weight.

13. A method of promoting antibacterial activity of immune effector cells, comprising the step of introducing into an infected mammalian subject to a therapeutically effective amount of granulocyte-macrophage colony stimulating factor (GM-CSF).

14. The method of claim 13, wherein the GM-CSF is of recombinant origin.

15. The method of claim 13, wherein the GM-CSF is purified to a specific activity of from about $6 \times 10^4$ to $1.5 \times 10^6$ colony forming units per microgram of protein as determined by bone marrow colony forming assay.

16. The method of claim 13, wherein the dosage of GM-CSF introduced into the body is approximately 0.05 µg to 500 µg per kilogram of body weight.

* * * * *

UNITED STATES PATENT AND TRADEMARK OFFICE
CERTIFICATE OF CORRECTION

PATENT NO. : 5,162,111
DATED : November 10, 1992
INVENTOR(S) : Kenneth H. Grabstein, et al It is certified that error appears in the above-indentified patent and that said Letters Patent is hereby corrected as shown below:

Column 1, line 21, insert a hyphen after the word gram in grampositive.

Column 3, line 11, italicize "in vitro"
Column 3, line 12, italicize "S. typhimurium"
Column 3, line 14, italicize "S. typhimurium"

Column 4, line 36, insert a hyphen after the word anti in antiinfective.

Column 6, line 47, delete (-) in the word phenol/-chloroform.

Column 7, line 5, delete the letter (e) in plasmides
Column 7, line 24, add a hyphen after the word well in welldefined Column 8, line 30, add a hyphen after the word well in welldefined Column 13, lines 36 and 37, delete the space between the words RN and ase to read RNase Column 14, line 49, insert --G-- after CCAAGGCC
Column 14, line 53, delete (t) from enought Signed and Sealed this Eleventh Day of January, 1994

Attest:

BRUCE LEHMAN

Attesting Officer    Commissioner of Patents and Trademarks